United States Patent [19]
Calabresi et al.

[11] Patent Number: 4,874,602
[45] Date of Patent: Oct. 17, 1989

[54] REDUCTION OF THE SEVERITY 3'-AZIDO-3'-DEOXYTHYMIDINE-INDUCED ANEMIA USING BENZYLACYCLOURIDINE

[76] Inventors: Paul Calabresi, 27 Glen Ave., Barrington, R.I. 02806; Michael C. Wiemann, 11 Villa Ave., Providence, R.I. 02906; Ming Y. W. Chu, Four Azalea Ct., Barrington, R.I. 02806

[21] Appl. No.: 158,463

[22] Filed: Feb. 22, 1988

[51] Int. Cl.$^4$ .................... A61K 31/70; A61K 31/505
[52] U.S. Cl. ........................................ 424/10; 514/50; 514/274; 514/814; 514/922
[58] Field of Search ................... 424/10; 514/922, 814

[56] References Cited
PUBLICATIONS

Niedzwicki et al., *Biochem. Pharmacol.*, 31:1857–1861, (1982).
Chu et al., *Cancer Res.*, 44:1852–1856, (1984).

*Primary Examiner*—Douglas W. Robinson
*Assistant Examiner*—Richard Kearse
*Attorney, Agent, or Firm*—Smith & Schnacke

[57] ABSTRACT

A method of reducing anemia caused by the administration of 3'-azido-3'-deoxythymidine to an animal which comprises treating said animal with a compound which inhibits the enzyme uridine phosphorylase in order to increase cellular uridine levels is disclosed. A particularly-effective compound is 5-benzylacyclouridine.

5 Claims, No Drawings

REDUCTION OF THE SEVERITY 3'-AZIDO-3'-DEOXYTHYMIDINE-INDUCED ANEMIA USING BENZYLACYCLOURIDINE

BACKGROUND OF THE INVENTION

3'-Azido-3'-deoxythymidine (AZT) is the only drug which is commercially available for the treatment of the acquired immune deficiency syndrome (AIDS) or symptomatic advanced AIDS-related complex (ARC). AZT inhibits the human immunodifficiency virus reverse transcriptase.

The main toxic affect of AZT in patients receiving the drug is severe anemia, often associated with megaloblastic bone marrow (Yarchoan, et al., Lancet, 1986, 1:575.

AZT was found to consistently inhibit granulocyte macrophage colony forming cells and erythroid burst-forming cells in dose-dependent fashion in vitro (Sommadossi and Carlisle, Antimicrobial Agents Chemo., 1987, 31:453–454). The authors concluded that since prolonged AZT therapy will probably be required by an AIDS patient, such patients will be subject to increased myelosuppression leading to increased risk of opportunistic infections.

In studies carried out in vitro to "rescue" human bone marrow progenitor (HBMP) cells using potential rescue agents, Sommadossi, et al., found that uridine and cytidine could reverse the toxic effect of AZT in HBMP cells.

While uridine is able to reverse the toxic effect of AZT on HBMP cells in vitro, unfortunately, uridine is deleterious to humans when given in vivo. When uridine is administered to a patient in an intermittant schedule, it is rapidly eliminated from the plasma. Continuous infusion of uridine is associated with rapid and potentially dangerous rises in body temperature. (See van Groeninger, et al., Cancer Treatment Rept., 70:745–750, 1986.)

The acyclouridine 5-benzylacylouridine (BAU) is an inhibitor of the enzyme uridine phosphorylase which is responsible for the cleavage of uridine to uracil. (See Niedzwicki, et al., Biochem. Pharmacol., 1982, 31:1857-1861). BAU also inhibits the cleavage of the antineoplastic 5-fluoro-2'-deoxyuridine (Fd Urd) used in cancer chemotherapy because of its inhibition of the action of uridine phosphorylase (See Chu, et al., Cancer Res., 1984, 44:185256.)

It has been found that concomitant administration of BAU to animals receiving AZT reduces the severity of AZT-induced anemia. None of the animals treated with a combination of BAU/AZT developed severe suppression of hemoglobin or hematocrit. Administration of BAU also produced a rise in the reticulocyte count, hemoglobin and hematocrit of animals which had previously been made anemic by administration of AZT.

SUMMARY OF THE INVENTION

The invention is directed to a method of reducing anemia produced by the administration of AZT to an animal which comprises administering to said animal an effective anemia inhibiting amount of 5-benzylacyclouridine.

DETAILED DESCRIPTION OF THE INVENTION

The invention is directed to a method of inhibiting anemia caused by the administration of AZT to an animal which comprises administering to said animal an effective anemia-inhibiting amount of 5-benzylacyclouridine. The invention is further directed to a pharmaceutical composition comprising as the active pharmaceutical agent the compound 5-benzylacyclouridine in combination with a pharmaceutically acceptable carrier or diluent.

The preparation of 5-benzylacyclouridine is described in Niedzwicki, et al., Biochem. Pharmacol., 1982, 31:1857–1861.

Although the use of 5-benzylacyclouridine in the method of the invention is specifically described herein, any pharmaceutically acceptable compound which inhibits the enzyme uridine phosphoralase is expected to be useful in the practice of the method of the invention. Such compounds, as for example, 5-benzyl-1-[1,3-dihydroxy-2-propoxy)methyl]uracil and 5-(m-benzyloxybenzyl)-1-[1,3-dihydroxy-2-propoxy)methyl]uracil disclosed in U.S. Pat. 4,613,604 are contemplated for use in the method of the present invention.

3'-Azido-3'-deoxythymidine (AZT) is commercially available under the tradename "RETROVIR" from the Burroughs Welcomme Company, Research Triangle Park, NC. AZT should be administered to a patient in need of treatment according to the dosage and administration schedule set out in the Package Insert for said product. The recommended starting dose of AZT is 200 mg administered orally every 4 hours around the clock.

The following detailed examples provide further illustration of the practice of the method of the invention.

EXAMPLE 1

For oral administration, BAU was dissolved in water to achieve a final concentration of 0.3 mg/mL. For intraperitoneal administration, BAU was dissolved in dimethylsulfoxide (DMSO) to achieve final concentrations of 60, 100, or 120 mg/mL.

AZT produced by Burroughs Wellcome Co., 100 mg capsule, was dissolved in water 50° C. The solution was centrifuged at 15,000 rpm for 20 minutes. The supernatant was then diluted with water to achieve a final concentration of 1 mg/mL of AZT. The concentration was verified by spectrophotomer (maximum absorbance: 267y).

Female Balb/c mice, 6–12 weeks old, were purchased from the Animal Care Facility of the Roger Williams Cancer Center. The animals were randomly divided into eight groups. Six of the treatment protocols were performed in duplicate. Each group contains either four or five animals. The animals were weighed once weekly. Food and water was available ad libitum. Blood samples were obtained from the tail vein. The first blood sample was obtained on Day 0 and subsequent samples were obtained on Days 19, 27, 34 and 48 after the initiation of drug treatment. With each sampling, approximately 100 ul of blood was removed from each animal. The blood obtained from the animals in each group was pooled and analyzed by Coulter Counter. On each sample, hemoglobin, hematocrit, and white blood cell count was determined. The mean red cell volume was calculated. The Treatment Groups were as follows:

| | |
|---|---|
| Group 1 | Control |
| Group 2 | AZT administered in the drinking water (1 mg/mL). This corresponds to an |

|           | -continued                                    |
|-----------|-----------------------------------------------|
|           | administered dose of 145 mg/kg/day. DMSO was given ip, 0.01 mL/5 grams body weight, once weekly. |
| Group 3   | AZT administered in the drinking water (1 mg/mL). |
| Group 4   | BAU 240 mg/kg, ip, once weekly.               |
| Group 5   | AZT administered in the drinking water (1 mg/mL) and BAU 240 mg/kg, ip, once weekly. |
| Group 6   | AZT administered in the drinking water (1 mg/mL) and BAU 120 mg/kg, ip, twice weekly. |
| Group 7   | AZT administered in the drinking water (1 mg/mL) and BAU administered in the same container of drinking water (0.3 mg/mL). This corresponds to a daily administered dose of 43 mg/kg. The bioavailability of BAU administered orally was 80%. Therefore, the bioavailable dose of BAU administered to this group was 240 mg/kg/week. |
| Group 8   | AZT (1 mg/mL) administered in the drinking water and BAU 200 mg/kg/day, ip. BAU administration was begun on Day 27. |

The results are summarized in Table 1.

TABLE 1

| TREATMENT GROUP | 0 Hb | 0 Hct | 0 WBC | 19 Hb | 19 Hct | 19 WBC | 19 MCV* | 27 Hb | 27 Hct | 27 WBC | 27 MCV | 34 Hb | 34 Hct | 34 WBC | 34 MCV | 48 Hb | 48 HCT | 48 WBC | 48 MCV |
|---|---|---|---|---|---|---|---|---|---|---|---|---|---|---|---|---|---|---|---|
| 1 | 17.6 | 50.0 | 8.8 | 17.2 | 50.5 | 9.03 | 55.9 | 16.5 | 52 | 8.7 | 62.9 | 17.8 | 59 | 13.6 | 65.1 | 16.4 | 49.0 | 11.7 | 50.9 |
| 2 | 17.3 | 49.0 | 10.1 | 12.8 | 36.0 | 21.2 | 57.2 | 13 | 40 | 11.6 | 67.2 | 11.6 | 35 | 11.5 | 65.4 | 11.0 | 33 | 5.0 | 67.8 |
| 3 A | 17.2 | 43.0 | 8.4 | 15.0 | 43.0 | 17.7 | 65.4 | 13.6 | 43 | 13.6 | 70.3 | 13.9 | 42 | 13.3 | 61.8 | 13.2 | 34 | 5.6 | 55.5 |
| 3 B | 17.4 | 49.5 | 8.9 | 12.4 | 36.0 | 11.3 | 56.8 | 10.9 | 35 | 7.0 | 75.7 | 10.7 | 32 | 36.3 | 67.4 | 10.8 | 32.5 | 6.6 | 70.3 |
| 4 A | 18.6 | 52.0 | 8.8 | 17.5 | 50.0 | 10.8 | 56.2 | 16.2 | 51 | 6.6 | 67.5 | 17.2 | 50 | 7.9 | 57.0 | 16.6 | 49 | 6.4 | 52.8 |
| 4 B | 18.1 | 52.0 | 10.3 | 17.1 | 50.0 | 8.5 | 57.2 | 15.9 | 48 | 5.5 | 71 | 15.8 | 47 | 9.1 | 57.3 | 16.6 | 48 | 6.1 | 53.1 |
| 5 A | 17.4 | 50.0 | 9.2 | 14.6 | 42.0 | 23.1 | 60.9 | 14.1 | 44 | 7.9 | 80.4 | 14.2 | 43 | 11.4 | 68.7 | 12.5 | 39 | 5.7 | 77.8 |
| 5 B | 16.7 | 50.0 | 8.1 | 14.1 | 41.0 | 23.0 | 55.8 | 13.9 | 43 | 5.0 | 85.5 | 14.0 | 42 | 13.7 | 63.3 | 31.2 | 41 | 7.8 | 70.4 |
| 6 A | 18.0 | 51.0 | 10.1 | 14.8 | 43.0 | 19.6 | 60.8 | 13.8 | 44 | 10.2 | 66 | 14.6 | 45 | 23.1 | 66.4 | 13.1 | 40 | 6.6 | 67.9 |
| 6 B | 18.0 | 51.0 | 8.9 | 14.9 | 43.0 | 16.1 | 58.9 | 14.4 | 45 | 10.6 | 63.4 | 13.4 | 40 | 14.1 | 75.9 | 11.2 | 34 | 5.3 | 64.5 |
| 7 A | 17.5 | 50.0 | 7.6 | 14.7 | 42.0 | 15.7 | 57.3 | 14.4 | 43 | 8.2 | 59.4 | 15.3 | 45 | 23.4 | 68.8 | 13.0 | 42 | 8.3 | 68.5 |
| 7 B | 17.8 | 49.0 | 10.7 | 14.9 | 44.0 | 22.0 | 59.5 | 12.9 | 40 | 9.8 | 60.1 | 13.7 | 40 | 8.6 | 55.4 | 12.2 | 38 | 10.4 | 69.6 |
| 8 A | 18.0 | 50.0 | 9.7 | 13.8 | 38.0 | 15.5 | 54.7 | 11.7 | 36 | 7.9 | 58.5 | 10.7 | 31 | 21.4 | 59.0 | 13.3 | 40 | 8.0 | 67.7 |
| 8 B | 18.2 | 51.0 | 11.4 | 14.1 | 42.0 | 14.0 | 60.0 | 10.8 | 35 | 10.8 | 70.9 | 11.7 | 36 | 19.5 | 54.3 | 11.6 | 36 | 8.1 | 70.2 |

*MCV = $\dfrac{\text{Hematocrit Value}}{\text{Red Blood Cell Count}} \times 10$

Reticulocyte counts were performed on blood samples from all of the groups described in Example 1 on Days 34 and 48. The results are summarized in Table 2.

TABLE 2

| Group No. | Day 34 | Day 48 |
|---|---|---|
| 1 | 1.7 | 0.4 |
| 2 | 2.0 | 0.4 |
| 3 A | 2.0 | 0.2 |
| B | 2.1 | 1.8 |
| 4 A | 1.4 | 0.65 |
| B | 1.0 | 0.10 |
| 5 A | 2.1 | 1.3 |
| B | 1.5 | 1.05 |
| 6 A | 1.2 | 1.6 |
| B | 1.5 | 2.55 |
| 7 A | 1.1 | 1.2 |
| B | 1.4 | 2.15 |
| 8 A | 1.2 | 5.0 |
| B | 1.5 | 5.6 |

As illustrated by the data from Group 8, administration of BAU to an already anemic animal resulted in the stimulation of the production of reticulocytes (young red blood cells) which should result in a subsequent rise in the hemoglobin of the animal. Thus, the administration of BAU to an animal receiving the AZT will reduce or eliminate AZT induced anemia. Further, the anemia which is caused by the administration of AZT to an animal can be reversed once the anemic condition is present.

The pharmaceutical compositions of the invention can be administered in a variety of dosage forms, e.g., orally, in the form of tablets, capsules, sugar, or film-coated tablets, liquid solutions or suspensions, rectally, in the form of suppositories, parenterally, e.g., intramuscularly or by intravenous injection or infusion. The preferred pharmaceutical composition of the invention is an intravenous composition. The exact dosage regimen of BAU which is useful in the compositions of the invention will depend on factors which would be recognized by the skilled artisan, e.g., the progreession of the AIDS disease, age, weight, other conditions of the patient and administration route.

The pharmaceutical compositions of the invention comprise BAU in association with a pharmaceutically acceptable excipient, which can be a carrier or a diluent. The pharmaceutical compositions of the invention are prepared following conventional methods and are administered in a pharmaceutically suitable form.

For example, the solid oral forms may contain, together with the active compound, diluents, e.g., lactose, dextrose, saccharose, cellulose, corn starcy or potato starch; lubricants, e.g., silica, talc, stearic acid, magnesium or calcium stearate, and/or polyethylene glycols; binding agents, e.g., starches, arabic gums, gelatin, methylcellulose, carboxymethylcellulose or polyvinly pyrrolidone; disaggregating agents, e.g., a starch, alginic acid, alginates or sodium starch glycolate, effervescing mixtures; dyestuffs; sweeteners; wetting agents, such a lecithin, polysorbates, laurylsulphates; and; in general, non-toxic and pharmacologically inactive substances used in pharmaceutical formulations. Said pharmaceutical preparations may be manufactured in known manner, for example, by means of mixing, granulating, tabletting, sugar-coating, or film-coating processes.

The liquid dispersions for oral administration may be, e.g., syrups, emulsions, and suspensions. The syrups may contain as carrier, for example, saccharose or saccharose with glycerine and/or mannitol and/or sorbitol; in particular a syrup to be administered to diabetic patients can contain as carriers only products not metabolizable to glucose, or metabolizable in very small amount to glucose, for example, sorbitol.

The suspensions and the emulsions may contain as carrier, for example, a natural gum, agar, sodium alginate, pectin, methylcellulose, carboxymethylcellulose, or polyvinyl alcohol. The suspensions or solutions for intramuscular injections may contain together with the active compound a pharmaceutically acceptable carrier, e.g., sterile water, olive oil, ethyl oleate, glycols, e.g., propylene glycol, and if desired, a suitable amount of lidocaine hydrochloride.

The solutions for intravenous injections or infusions may contain a carrier, for example, sterile water or preferably they may be in the form of sterile, aqueous, isotonic saline solutions.

The suppositories may contain together with the active compound a pharmaceutically acceptable carrier, e.g., cocoa butter, polyethylene glycol, a polyoxyethylene sorbitan fatty acid ester surfactant or lecithin.

Having described the invention in detail and by reference to the preferred embodiments thereof, it will be apparent that modifications and variations are possible without departing from the spirit and scope of the invention defined in the appended claims.

What is claimed is:

1. A method of reducing anemia caused by the administration of 3'-azido-3'-deoxythymidine to an animal which comprises administering to said animal an effective anemia-inhibiting amount of 5-benzylacyclouridine.

2. A method according to claim 1, wherein said animal is a human.

3. A method according to claim 1, wherein 3'-azido-3'-deoxythymidine is administered orally and 5-benzylacyclouridine is administered orally, intramuscularly or intravenously.

4. A method according to claim 3, wherein 5-benzyacyclouridine is administered intravenously.

5. A pharmaceutical composition comprising a therapeutically effective amount of 3'-azido-3'-deoxythymidine and a therapeutically effective anemia-inhibiting amount of 5-benzyacyclouridine in combination with a pharmaceutically acceptable carrier or diluent.

* * * * *

Notice of Adverse Decisions in Interference

In Interference No. 102,448, involving Patent No. 4,874,602, Paul Calabrest, Michael C. Wiemann, Ming Y. W. Chu, REDUCTION OF THE SEVERITY OF 7'-AZIDO-3'-DEOXYTHYMIDINE-INDUCED ANEMIA USING BENZYLACYCLOURIDINE, final judgement adverse to the patentees was rendered Aug. 26, 1991, as to claims 1-5.

*(Official Gazette Oct. 22, 1991)*